United States Patent [19]
Paduano et al.

[11] Patent Number: 5,709,004
[45] Date of Patent: Jan. 20, 1998

[54] TOOTHBRUSH WITH DEVICE FOR CLEANING THE TONGUE

[76] Inventors: Guido Paduano; Elisabetta Rossi, both of Via Roma No.12, 22067 Missaglia, Como, Italy; Simone Zilli, Via Montegrappa No.1, Frazione Usigliano, 56035 Lari, Pisa, Italy, 56035

[21] Appl. No.: 680,375

[22] Filed: Jul. 15, 1996

[30] Foreign Application Priority Data

Jul. 20, 1995 [IT] Italy .................... FI95A0167

[51] Int. Cl.⁶ .................... A46B 9/04; A61B 17/24
[52] U.S. Cl. .................... 15/111; 15/110; 15/167.1; 132/309; 606/161; D4/108; D24/146
[58] Field of Search .................... 15/110, 111, 167.1; 132/309; 606/161; D4/108; D24/146

[56] References Cited

U.S. PATENT DOCUMENTS

| | | | |
|---|---|---|---|
| 856,711 | 6/1907 | Lees | 606/161 |
| 1,470,710 | 10/1923 | Davis | 15/167.1 |
| 1,521,425 | 12/1924 | Buckley | 132/309 X |
| 2,405,029 | 7/1976 | Gallanty et al. | 606/161 |
| 2,651,068 | 9/1953 | Seko | 606/161 X |
| 5,061,272 | 10/1991 | Reese | 606/161 |
| 5,282,814 | 2/1994 | Srivastava | 606/161 |

FOREIGN PATENT DOCUMENTS

| | | | |
|---|---|---|---|
| 142729 | 9/1935 | Austria | 15/167.1 |
| 734846 | 10/1932 | France | 606/161 |
| 592757 | 2/1934 | Germany | 15/167.1 |
| 3-286708 | 12/1991 | Japan | 15/167.1 |
| 2 027 347 | 2/1980 | United Kingdom . | |

*Primary Examiner*—Mark Spisich
*Attorney, Agent, or Firm*—McGlew & Tuttle

[57] ABSTRACT

The toothbrush includes a handle (1) with a head (3) furnished with bristles (5) and a device for cleaning the surface of the tongue. The handle (1) is composed of two parts (1A, 1B) joined by a thin, flexible, arc-shaped strip (7) at the base of the handle (1) opposite the head (3). The thin, flexible strip (7) serves as a scraper for cleaning the tongue.

14 Claims, 4 Drawing Sheets

Fig. 4 Fig. 5 Fig. 6
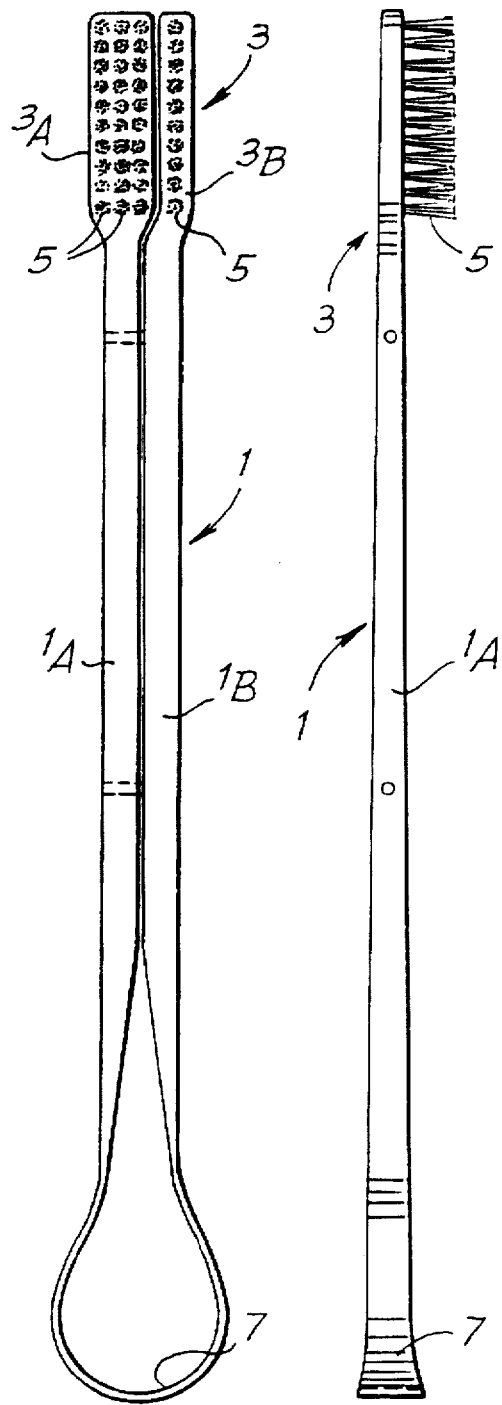
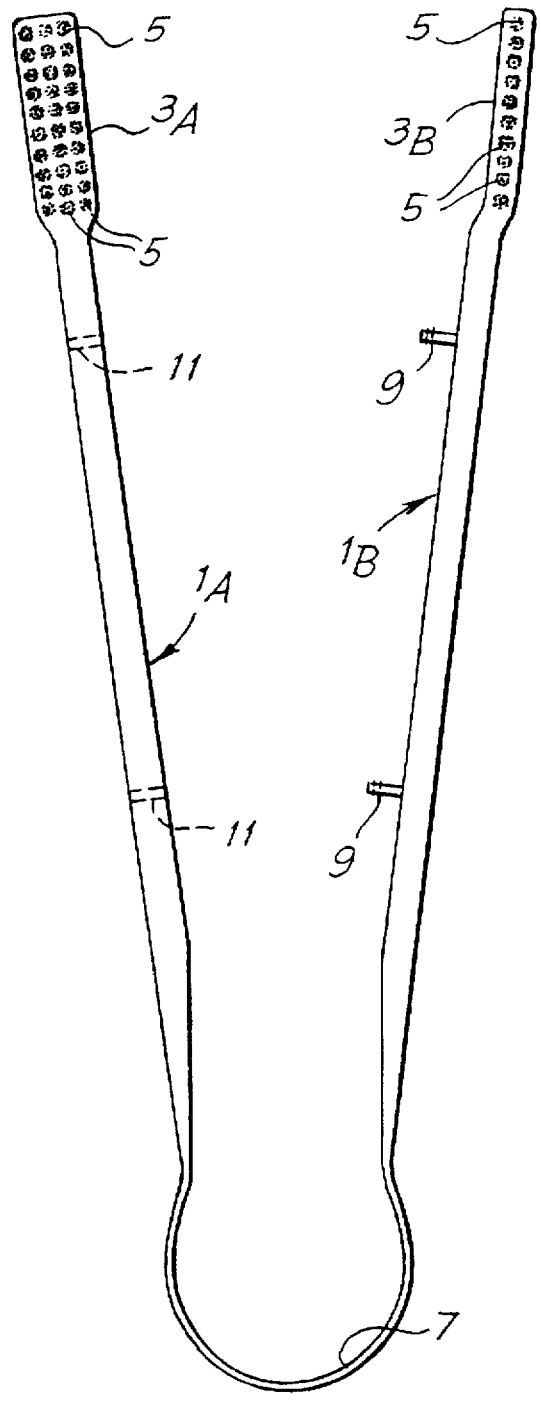

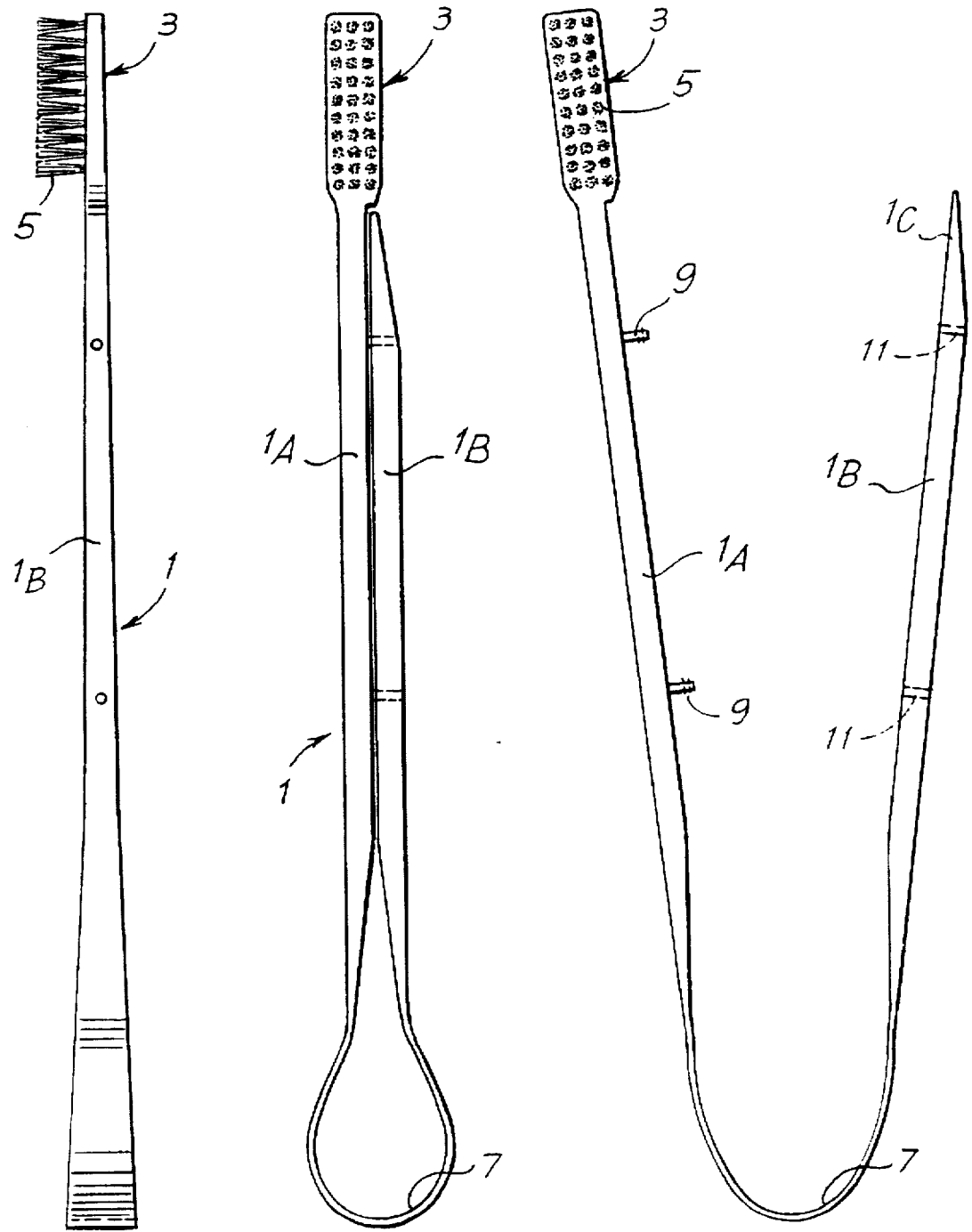

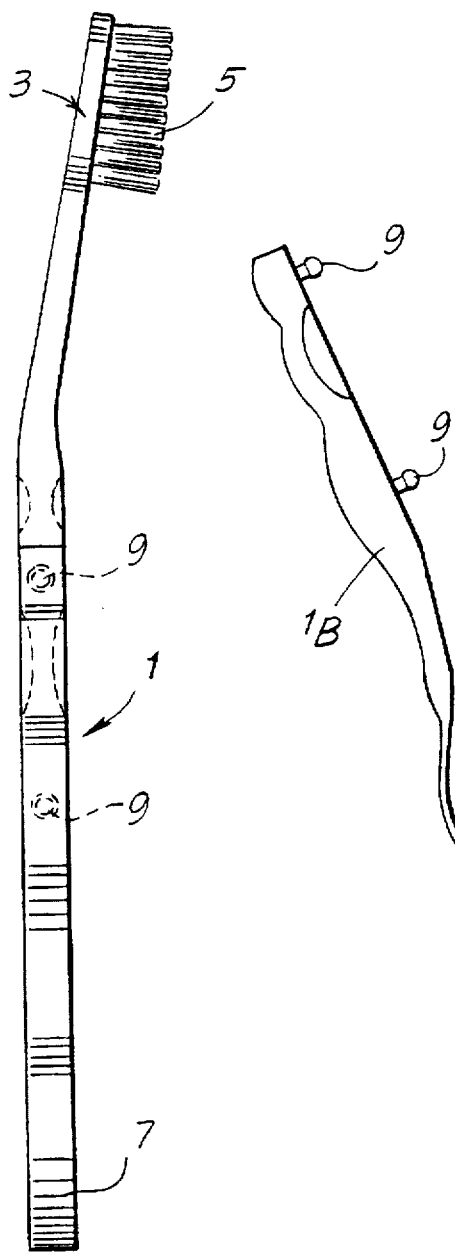
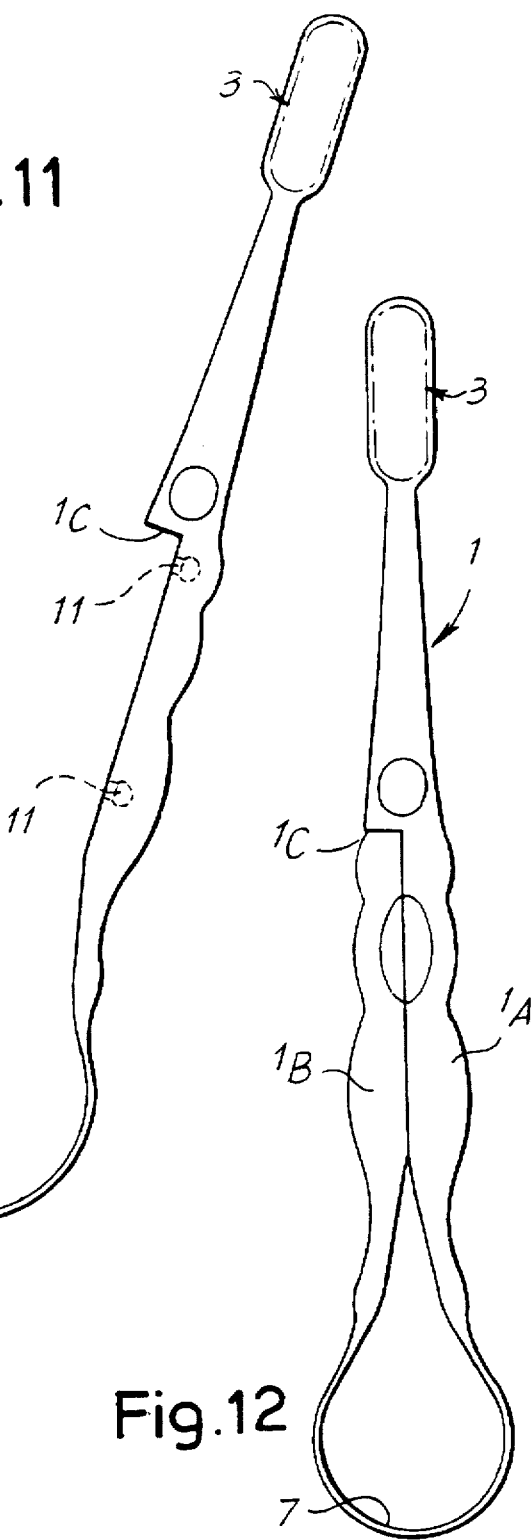

TOOTHBRUSH WITH DEVICE FOR CLEANING THE TONGUE

FIELD OF THE INVENTION

The invention refers to a toothbrush with a device combined with the handle for cleaning (by scraping) the surface of the tongue.

BACKGROUND OF THE INVENTION

It is well known that the accumulation of material on the surface of the tongue can be the source of various problems. The fermentation of food deposits can cause bad odors as well as create an environment conducive to tooth decay.

For this reason various instruments have been invented to clean the upper surface of the tongue through the mechanical action of "scraping". In U.S. Pat. No. 5,282,814 such a device is described with a kind of blade connected to a double handle. The blade, in plastic or similar material, is passed over the surface of the tongue in a forward-backward motion to remove the coating.

A similar device is described in U.S. Pat. No. 5,061,272, which discloses an instrument having a C-shaped cross section for the removal of deposits from the surface of the tongue.

In GB-A-2,027,347 another instrument is described as made with a flexible blade placed inside a slot in the toothbrush handle. This device has the advantage of being part of the toothbrush, but it has serious disadvantages, such as the difficulty in making the slot for the flexible blade in the handle, thereby increasing production costs; the inconvenience of extracting and inserting the blade; and it is unhygenic, as the slot holding the blade can easily accumulate various kinds of residue difficult to remove because of its shape.

OBJECTS OF THE INVENTION

The object of the invention is the manufacture of an instrument for oral hygiene, which is not affected by the above mentioned disadvantages and which is, in particular, both a toothbrush and a device for cleaning the tongue.

SUMMARY OF THE INVENTION

This and other objects and advantages, which will be evident to those skilled in the field from the following text, are obtained from a brush whose handle consists of two longitudinal sections joined by a thin, flexible arc-shaped strip at the end of the handle opposite the head, the said thin, flexible strip serving as an instrument for cleaning the tongue through scraping.

The thin, flexible strip can easily be made from the same material (synthetic resin, for example) as the two sections of the handle and the head containing bristles. Thus, without the need for complex slots or cavities in the handle, the brush can be made simply and economically by injection molding. The material and the cross section of the handle sections and of the intermediate flexible strip should be chosen to give the handle sufficient strength, while leaving the strip sufficiently flexible to allow the coupling of the two parts of the handle and the separation of them in order for the strip to be employed as a scraper for cleaning the tongue, the two sections of the handle then serving as grips.

In a particularly advantageous embodiment of the brush according to the invention, also the head is formed in two separable sections, each one integral with its respective section of the handle. It is preferable to have the two sections of the head different from each other—one thinner, for example, with a single row of bristles. The thinner section of the head can be advantageously used for cleaning areas of the oral cavity otherwise difficult to reach.

Other advantageous features of the invention are set forth in the dependent claims.

BRIEF DESCRIPTION OF THE DRAWINGS

The invention will be more readily understood by reading the following description and observing the accompanying drawings, which illustrate practical and non-limiting embodiments of said invention. In the drawings:

FIGS. 4 through 6 show a second embodiment of the brush in a closed frontal view, a side view and an open frontal view, respectively;

FIGS. 7 through 9 show a third embodiment in views similar to FIGS. 4, 5, 6; and FIGS. 10 through 12 show a third embodiment of the toothbrush.

DETAILED DESCRIPTION OF EMBODIMENTS OF THE INVENTION

Figure 2:
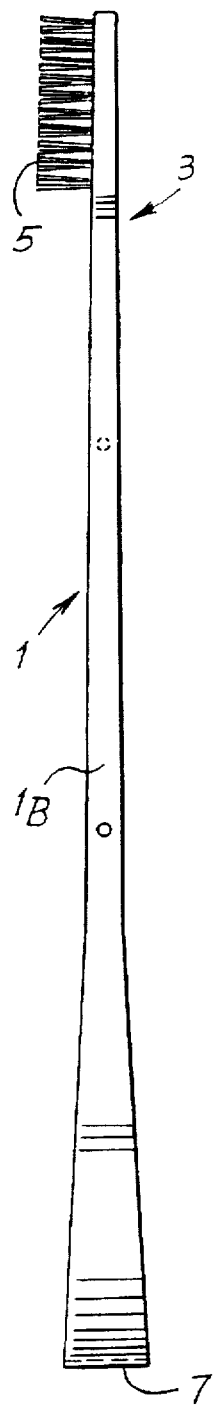
FIG. 2 shows a side view according to line II—II of FIG. 1.
Figure 1:
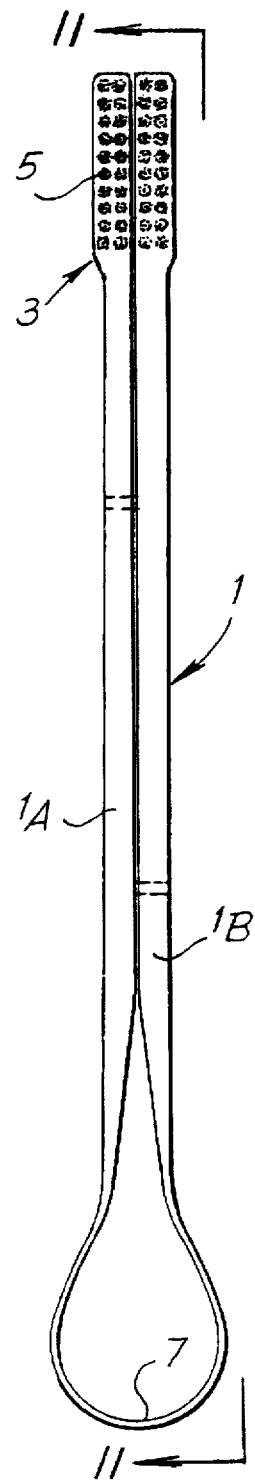
FIG. 1 shows a frontal view of a first embodiment of the brush according to the invention.
Figure 3:
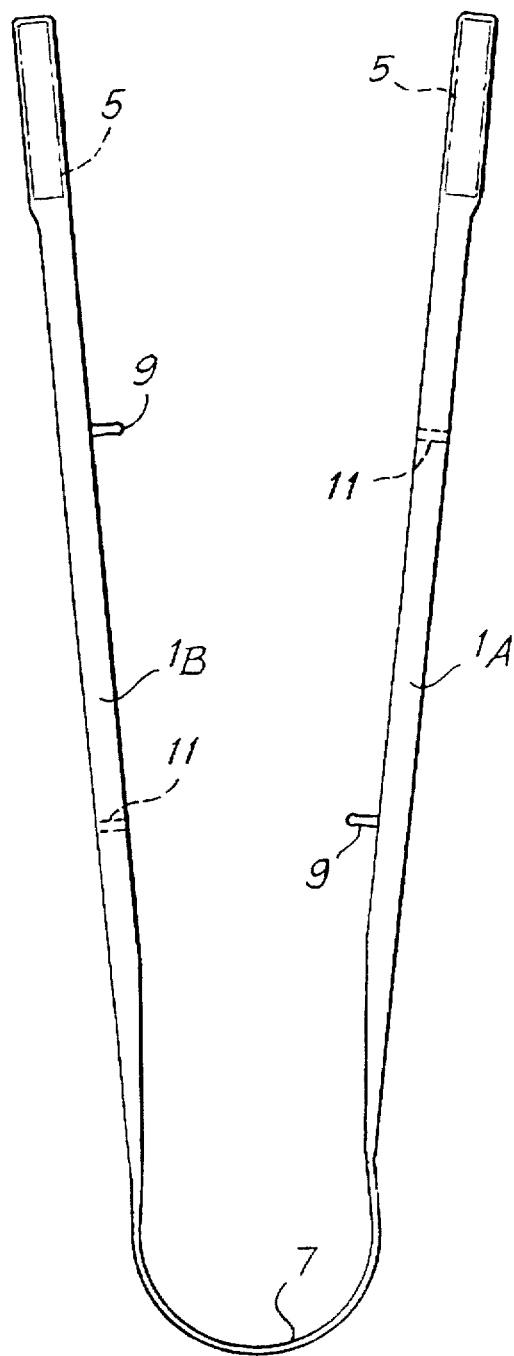
FIG. 3 shows a back view of the brush in open position.

FIGS. 1 through 3, represent the toothbrush with a handle 1 and a head 3 with bristles 5. Both the handle 1 and the head 3 are made of two separate sections (which are symmetrical in the example of FIGS. 1 to 3), which are separated along a plane parallel to the handle and which are joined at the end opposite the head by a thin, flexible, arc-shaped strip 7 with sufficiently sharp edges, uniting sections 1A and 1B to form the handle 1.

Opening the two sections 1A and 1B of the handle (FIG. 3) the flexible strip 7 forms a kind of scraper for cleaning by scraping the upper surface of the tongue. The two sections 1A and 1B of the brush handle form two grips for the instrument.

Therefore, besides the normal function of cleaning the teeth when closed as in FIG. 1, when once opened (FIG. 2) this instrument can be used as a "tongue-scraper" to remove easily from the tongue's surface bacterial coating, food residues, or other things such as condensations and nicotine from cigarettes, etc., that daily form, or are deposited, on it.

The two sections 1A, 1B of the handle 1 can be joined by a system of pins 9 and corresponding slots 11 or the like.

FIGS. 4 through 6 show a toothbrush analogous to that of FIGS. 1 through 3, but different in that the head 3 is divided into two asymmetrical sections 3A and 3B. Section 3A is wider and displays (in the illustrated example) a triple row of bristles. In section 3B the head has only one row of bristles and is useful for cleaning areas difficult to reach in the oral cavity. The bristles can also be more sparse for easier access to spaces between the teeth.

In FIGS. 7 through 9 another embodiment of the invention is shown in which the head 3 is not divided into two sections; only the handle 1 is formed by the two parts 1A, 1B that are able to be joined or separated. The end 1C of section 1B of the handle can be provided with a seat for an intradental cleaning device or the like, or with a rubber tip for massaging the gums, etc.

FIGS. 10 to 12 show a further embodiment of the invention. The same reference numbers are used to indicate the same or corresponding parts of the brush. Similarly to the embodiment of FIGS. 7 through 9, the toothbrush of this embodiment has a handle 1 which is formed by two sections 1A, 1B, one of which is provided with the head 3. The central portion of the handle is shaped for better gripping. The shorter portion 1B of the handle is housed in an indentation 1C of portion 1A forming a seat.

It is to be understood that the drawings show only examples provided solely as a practical demonstration of the invention, and that this invention may be varied in its forms and dispositions without departure from the scope of the concept underlying the invention.

We claim:

1. A toothbrush comprising:

an elongated handle with a head equipped with bristles attached to an end thereof, and a device for cleaning the surface of the tongue, wherein said handle is composed of two sections joined by a thin, flexible, arc-shaped strip used for cleaning the tongue, placed at the end of the handle opposite said head, a first section of said two sections of said handle including a pin, and a second section of said two sections of said handle defining a slot for receiving said pin and joining said first and second sections of said handle.

2. Toothbrush according to claim 1, wherein said head is made in two separable sections, each one of said separable sections being equipped with bristles and integral with a respective one of said handle sections.

3. Toothbrush according to claim 2, wherein the two sections of said head, in which the head is divided, are symmetrical.

4. Toothbrush according to claim 2, wherein the two sections of said head, in which the head is divided, are different from each other, one section being thinner than the other.

5. Toothbrush according to claim 1, wherein said head is not divisible and is integral to an end of one of the sections of the handle.

6. Toothbrush according to claim 5, wherein a free end of the other section of said handle has a seat for an accessory for oral hygiene, said accessory being selected from the group consisting of an intradental cleaning means and a gum massaging means.

7. Toothbrush according to claim 1, wherein the pin and slot of said two sections of the handle form separable connection means.

8. A toothbrush comprising:

an elongated handle having first and second sections, said first and second sections having first and second ends;

a flexible arc-shaped strip connected to said second ends of said first and second sections, an edge of said arc shaped strip forming a scraper means for removing material from a surface of a tongue;

a head connected to said first end of one of said sections of said handle, said head, said first and second sections, and said arc-shaped strip being formed in a single piece of injection molded synthetic plastic, said head including bristles;

connection means for connecting said first and, second sections together in a side-by-side arrangement to form said handle.

9. A toothbrush in accordance with claim 8, wherein:

said head is formed in first and second parts with said first part being connected to said first end of said first section and said second part being connected to said first end of said second section.

10. A toothbrush in accordance with claim 9, wherein: said first part of said head is wider than said second part of said head.

11. A toothbrush in accordance with claim 8, further comprising:

accessory means connected to said first end of the other section of said handle, said accessory means performing an oral hygiene function separate from said bristles.

12. A toothbrush in accordance with claim 11, wherein:

said accessory means being selected from the group consisting of an intradental cleaning means and a gum massaging means.

13. A toothbrush in accordance with claim 8, wherein:

said connection means is formed as a single piece with said head, said first and second sections, and said arc-shaped strip.

14. A toothbrush comprising:

an elongated handle having first and second sections, said first and second sections having first and second ends, said first section defining an indentation at said first end;

a flexible arc-shaped strip connected to said second ends of said first and second sections, an edge of said arc shaped strip forming a scraper means for removing material from a surface of a tongue;

a head connected to said first end of one of said sections of said handle, said head including bristles;

connection means for reversibly connecting said first end of said second section to said first section in a side-by-side arrangement to form said handle, said connection means placing said first end of said second section in said indentation of said first end of said first section in said side-by-side arrangement.

* * * * *